United States Patent [19]

Arenas et al.

[11] Patent Number: 4,676,249
[45] Date of Patent: Jun. 30, 1987

[54] MULTI-MODE GUIDEWIRE

[75] Inventors: Alvaro E. Arenas; Caius C. Hooker, both of Miami, Fla.

[73] Assignee: Cordis Corporation, Miami, Fla.

[21] Appl. No.: 864,499

[22] Filed: May 19, 1986

[51] Int. Cl.⁴ .............................................. A61B 6/00
[52] U.S. Cl. .................................... 128/657; 128/772; 604/164; 604/170; 604/282
[58] Field of Search .................. 128/657, 772; 604/95, 604/170, 280, 282, 164, 166

[56] References Cited

U.S. PATENT DOCUMENTS

| | | | |
|---|---|---|---|
| 2,024,982 | 1/1937 | Scott | 128/348.1 |
| 3,906,938 | 9/1975 | Fleischhacker | 604/170 |
| 4,003,369 | 1/1977 | Heilman et al. | 128/772 |
| 4,215,703 | 8/1980 | Willson | 604/95 |
| 4,271,847 | 6/1981 | Stokes | 128/786 |
| 4,454,888 | 6/1984 | Gold | 128/786 |
| 4,456,017 | 6/1984 | Miles | 128/772 |
| 4,498,482 | 2/1985 | Williams | 128/786 |
| 4,548,206 | 10/1985 | Osborne | 128/772 |
| 4,554,929 | 11/1965 | Samson et al. | 128/772 |

FOREIGN PATENT DOCUMENTS 193885   1/1965   Sweden .

*Primary Examiner*—Kyle L. Howell
*Assistant Examiner*—Randy Cetrin
*Attorney, Agent, or Firm*—Henry W. Collins; Thomas R. Vigil

[57] ABSTRACT

The multi-mode guidewire selectively allows the creation of varying degrees of flexibility at varying locations of the guidewire. An elongate coiled wire body of the guidewire is capable of assuming an arcuate shape adjacent to its capped distal end. The coiled wire body may be made less flexible by a curve control core wire which is positionable by means of a knob at its proximal end. The curve control core wire includes a region of moderate flexibility in its distal region which can be stiffened by a stiffening member. The stiffening member is positionable by a handle located at its proximal end. A method of advancing a catheter and the guidewire includes selecting a most advantageous mode of use of the guidewire for advancement.

12 Claims, 6 Drawing Figures

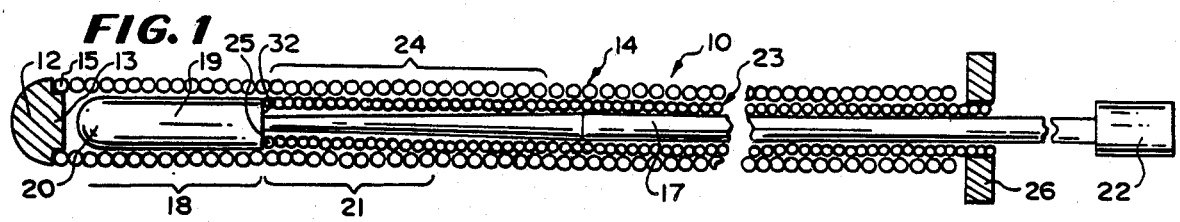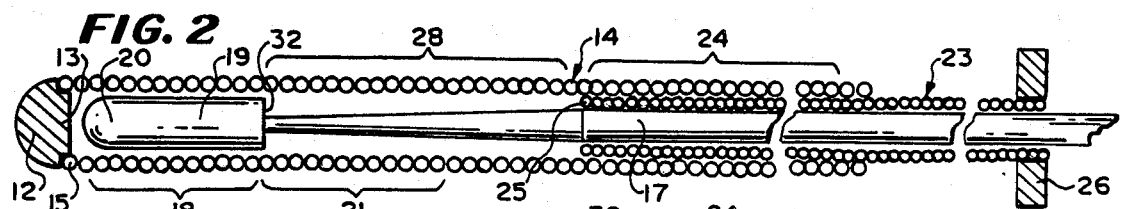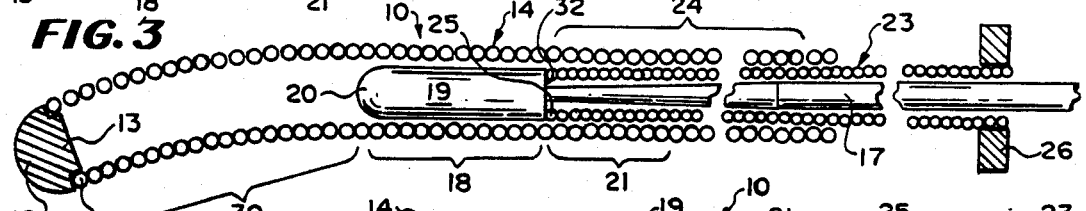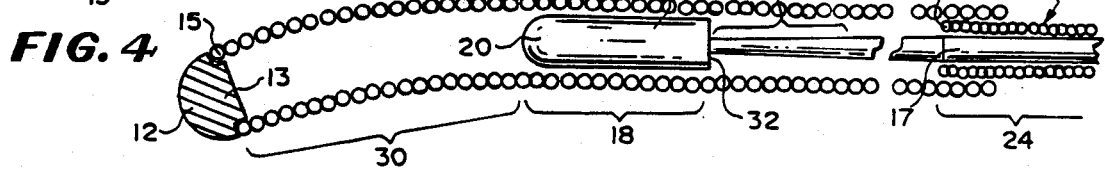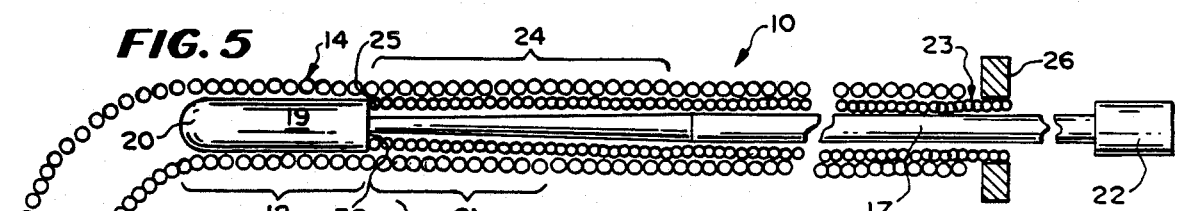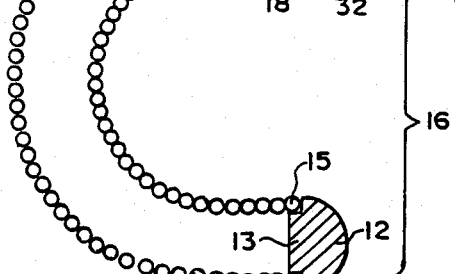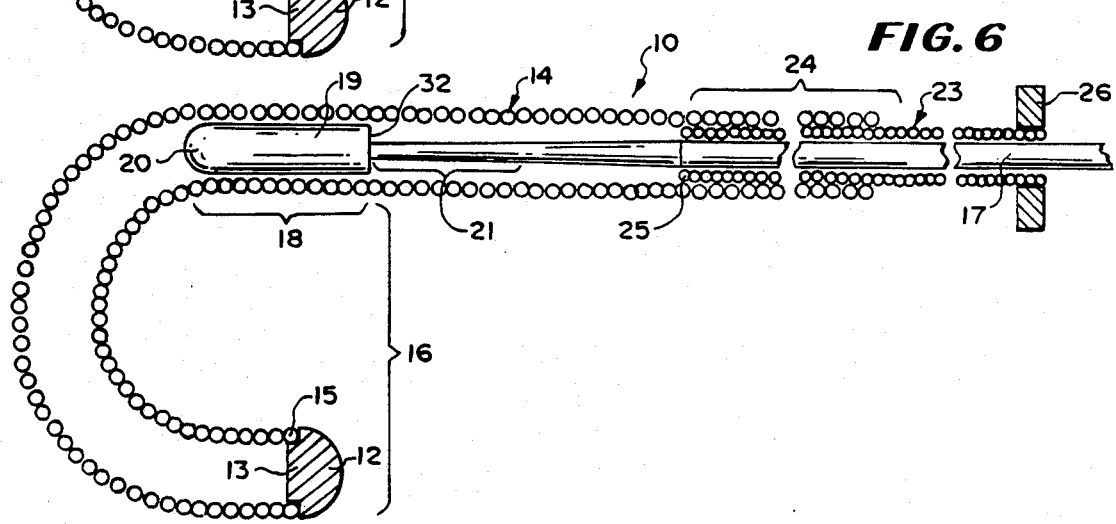

MULTI-MODE GUIDEWIRE

BACKGROUND OF THE INVENTION

Heretofore coiled spring guidewires have been widely used for facilitating insertion of catheters into a blood vessel. Catheters are generally hollow, flexible tubes generally used to convey fluid to or from a desired body location. Some catheters are capable of being preformed to various shapes which best conform to their anticipated environment.

Often, a catheter insertion procedure is followed. Such procedure includes the first step of inserting an obdurated hollow needle into the body with the object of locating the needle tip in the target vessel. The location of this needle tip is confirmed by removing the obdurator while preparing to insert a coiled spring through the open hollow needle.

After insertion of the coiled spring guidewire through the needle, so that the guidewire extends a short distance distally beyond the needle tip, the needle is withdrawn proximally from the body and the guidewire.

A dilator, of greater diameter and length than the needle, is then substituted for the needle by being inserted into the body surrounding the guidewire, for nearly the length of the dilator.

Next the guidewire is advanced through the length of the dilator until it extends for a distance beyond it. At this point, the guidewire is relatively secure within the blood vessel and the dilator is withdrawn.

The catheter is next inserted over the guidewire and advanced slightly beyond the guidewire. A stylet or the equivalent is often inserted into the lumen defined by helical coils of the guidewire to impart a given form and a given stiffness to the guidewire and therefor to the catheter. The catheter and the guidewire, which may include a stylet, are further inserted into the vessel until an obstruction is encountered.

Obstructions are typically due to narrowing of the vessel opening or the vessel curvature. If the nature of the vessel obstruction is unknown or unanticipated, the catheter may be left in place while the guidewire, with stylet, is withdrawn and a radio opaque dye is injected to assist in determining the nature of the obstruction. A stylet of a differing stiffness or form may be employed to assist in navigating the obstruction.

After an obstruction is encountered, the guidewire is advanced only slightly beyond the distal end of the catheter where it can assume an arcuate shape appropriate to navigate the obstruction encountered. The guidewire is then caused to assume the arcuate shape and the obstruction is navigated. Then the catheter is advanced over the guidewire and the guidewire with the catheter are simultaneously advanced.

In most circumstances, the guidewire need not be advanced to the desired location before being withdrawn. The catheter frequently possesses sufficient longitudinal stiffness to allow direct manipulation of the catheter for the final stage of catheter insertion to the desired location.

It is desirable in using such a coiled spring guidewire to provide some means to allow the tip of the guidewire to deflect to facilitate movement of the guidewire around or through a curved or narrowed path in the vessel.

There have been a number of proposals for different tip constructions which will provide a deflectable tip in a coiled spring guidewire and related devices.

U.S. Pat. No. 4,554,929 to Samson et al. discloses a CATHETER GUIDE WIRE WITH SHORT SPRING TIP AND A METHOD OF USING THE SAME. The spring tip surrounds a reduced section extension of a guidewire shaft.

U.S. Pat. No. 4,498,482 to Williams discloses a TRANSVENOUS PACING LEAD HAVING IMPROVED STYLET. The stylet has a constant diameter at its proximal end, a ball at its distal end and a tapered section in the transition of the stylet from a constant diameter to the ball portion.

U.S. Pat. No. 4,456,017 to Miles discloses a COILED SPRING GUIDE WITH DEFLECTABLE TIP. Its core wire has a reduced section at its distal end which is permanently, and eccentrically, affixed to a head member. Proximal movement of the core wire causes the guide to assume an arcuate shape.

U.S. Pat. No. 4,454,888 to Gold discloses a CARDIAC PACING LEAD WITH CURVE RETAINER. A flat spring near its distal end causes the lead to assume a J-shape when a stylet is withdrawn from that portion of the lead.

U.S. Pat. No. 4,271,847 to Stokes discloses a TEMPORARY ADJUSTABLE BIPOLAR LEAD including a coaxial sliding pacing lead for establishing a connection between a chamber of a heart and a pulse generator.

U.S. Pat. No. 2,024,982 to Scott discloses a SURGICAL INSTRUMENT including a flat tapered stylet.

United Kingdom Patent Application No. 2,064,963A describes a STYLET having a tapered portion terminating at a ball in its distal end and is related to U.S. Pat. No. 4,498,482 referred to above.

Swedish Pat. No. 193885 discloses A CATHETER INTENDED FOR INTRAVASCULAR CATHERIZATION having an arcuately curved distal end which is straightenable by an inserted stylet. The stylet has a rounded cylindrical distal end portion.

However, none of the foregoing patent publications disclose a multi-mode guidewire which provides a varying degree of flexibility at varying longitudinal locations of the guidewire.

SUMMARY OF THE INVENTION

According to the invention there is provided a a multi-mode guidewire comprising an elongate flexible coiled wire body including coils helically wound about a coil axis to define a longitudinally extending lumen therein. The coiled wire body has a proximal end and a distal end and is capable of assuming an arcuate shape adjacent its distal end. A cap is mounted on the distal end of the coiled wire body. An elongate curve control core wire is disposed within the lumen of the coiled wire body and is slidable in the wire body along the coil axis. The curve control core wire has a proximal end and a distal end and is sufficiently stiff in a distal region to overcome the predisposition of the coiled wire body to assume the arcuate shape adjacent the body's distal end. Also the curve control core wire has a moderately flexible portion just proximal of the stiff portion of the distal region of the curve control core wire. A knob is fastened to the proximal end of the curve control core wire for facilitating control of the relative position of the distal end of the curve contol core wire with respect to the cap. An elongate stiffening member is disposed within the lumen of the coiled wire body and has a proximal end and a distal end. The stiffening member is slidably positonable in the wire body along the coil axis with respect to the distal end of the curve control core wire and is longitudinally stiff at its distal region to stiffen the moderately flexible region of the curve control core wire when the stiffening member is in near engagement with the stiff distal regon of the curve control core wire. A member is fastened to the proximal end of the stiffening member for facilitating control of the relative positon of the distal end of the stiffening member with respect to the distal end of the curve control core wire.

Further according to the invention there is provided a method for inserting a catheter through a body vessel to reach a body cavity using the multi-mode guidewire described above. The method of insertion comprises: inserting the guidewire and catheter into a blood vessel in a conventional manner; advancing the catheter and guidewire in the blood vessel utilizing a substantially straight relatively inflexible mode of use of the guidewire or a substantially straight moderately flexible mode of use of the guidewire until a bend in the blood vessel is reached; selecting an advancement mode for the guidewire depending on the vessel configuration adjacent the distal region consisting of one of the following modes of use: a partially curved relatively inflexible mode, a partially curved moderately flexible mode, a curved relatively inflexible mode, and a curved moderately flexible mode; further advancing the guidewire distally in the vessel as long as the mode selected is the most appropriate manner for advancement; advancing the catheter; returning to the selecting step; and repeating the selecting step and the advancing step and subsequent steps until a body cavity is approached.

BRIEF DESCRIPTION OF THE DRAWINGS

FIG. 1 is a longitudinal cross-sectional view of the multi-mode guidewire of the present invention in a straight rigid mode with portions broken away.

FIG. 2 is a longitudinal cross-sectional view of the multi-mode guidewire in its straight flexible mode of use with portions broken away.

FIG. 3 is a longitudinal cross-sectional view of the multi-mode guidewire in a partially curved inflexible mode of use with portions broken away.

FIG. 4 is a longitudinal cross-sectional view of the multi-mode guidewire in a partially curved flexible mode of use with portions broken away.

FIG. 5 is a longitudinal cross-sectional view of the multi-mode guidewire in its curved inflexible mode of use with portions broken away.

FIG. 6 is a longitudinal cross-sectional view of the multi-mode guidewire in its curved flexible mode of use with portions broken away.

DESCRIPTION OF THE PREFERRED EMBODIMENT

FIG. 1 is a longitudinal cross-sectional view of the multi-mode guidewire 10 of the present invention. The multi-mode guidewire 10 is a generally elongate device adapted to be guided through a natural tortuous conduit of the body, such as a blood vessel, usually towards a natural cavity of the body, such as a heart. The guidewire 10 provides varying degrees of transverse flexibility in varying longitudinal locations of the guidewire 10 and is capable of assuming an arcuate shape near its distal end where a cap 12 is located. The distal end of the cap 12 is generally hemispherical and a short cylindrical stem 13 extends proximally from the cap 12. The hemispherical shape of the cap 12 is well suited to guide the device 10 through a vessel while avoiding undue trauma to the wall of the vessel. The cap 12 is in engagement with a distal end of an elongate flexible coiled wire body 14.

The cylindrical stem 13 of the cap 12 is surrounded by the distal end coil 15 of the coiled wire body 14. A conventional ribbon, or safety wire (not shown), is affixed to the cylindrical stem 13 of cap 12, the distal end coil 15 of the coiled wire body 14, a proximal end coil of the coiled wire body 14 and an annular retainer (not shown) at the proximal end of the coiled wire body 14. The safety wire prevents potential disengagement of the cap 12 from the coiled wire body 14 and undue elongation of the coiled wire body 14.

The coiled wire body 14 is helically wound from steel or plastic wire stock about a concentric coil axis at the center of a lumen defined by the coiled turns. Typically, the wire stock is wound around a mandrel. The wire stock should be compatible with the body and is preferably plastic (Teflon TM or polymid) coated stainless steel. Among other features, the plastic coating enchances lubricity between the coiled wire body 14 and the vessel as well as lubricity among cooperative elements of the guidewire 10.

The coiled wire body 14 is capable of assuming an arcuate J-shape adjacent its distal end to establish a flexible arcuate J portion 16 as illustrated in FIGS. 5 and 6.

When the guidewire 10 is deployed within an arterial vessel, counterflow of blood toward the proximal region of the guidewire 10 will tend to cause the guidewire 10 to assume an arcuate shape. Other forces such as gravity, the stiffness of cooperative elements of the guidewire 10 or a preformation of the coiled wire body 14 will affect the shape assumed. The coiled wire body 14 may be preconfigured to any desired shape by bending it beyond its elastic limit to the shape desired.

An elongate curve control core wire 17 is disposed within the lumen defined by the elongate coiled wire body 14 and is slidable within the coiled wire body 14 along the coil axis to a location in close proximity to the cap 12. The curve control core wire 17 is preferably fabricated from stainless steel. A distal region 18 of the curve control core wire 17 has a cylindrical portion 19 which tapers to a hemisphere end 20. The hemisphere end 20 of the curve control core wire 17 prevents forcing of the curve control core wire 17 through the coils of coiled wire body 14. The curve control core wire 17 is of uniform diameter through most of its proximal and middle regions. However, just proximal to the distal region 18 adjacent the cylindrical portion 19, the diameter of the curve control core wire 17 tapers forwardly to a narrower diameter at its junction with the cylindrical portion 19 to establish a region of moderate flexibility 21 adjacent the distal region 18 of the curve control core wire 17. The degree of flexibility thus imparted should be merely sufficient to overcome the ability of the coiled wire body 14 to assume an arcuate shape. The curve control core wire 17 is joined to a knurled knob 22 at its proximal end.

The knob 22, as shown, is generally cylindrical and facilitates rotational and longitudinal manipulation of the curve control core wire 17.

An elongate, generally tubular, stiffening member 23 is also received within the lumen defined by the coiled wire body 14. The stiffening member 23 is likewise slidably positionable within the coiled wire body 14 along the axis of the coiled wire body 14 relative to the distal hemisphere end 20 of the curve control core wire 17 and the cap 12. In its distal region 24, the stiffening member 23 must be longitudinally stiff to stiffen the moderately flexible region 18 of the curve control wire 17 when a distal coil end 25 of the stiffening member 23 is nearly engaged with the cylindrical portion 19 of the curve control core wire 17 as shown in FIGS. 1 and 4. Of course, full engagement between the tubular stiffening member 23 and the cylindrical portion 19 of the curve control core wire 17 further stiffens the moderately flexible region 18.

Preferably and as shown, the stiffening member 23 is defined by a helically coiled stainless steel wire. The coils of the stiffening member 23 should be very closely wound at least in the distal region 24 of the stiffening member 23 to provide sufficient stiffness to overcome the flexibility of the curve control core wire 17 in the moderately flexible region 21 thereof. In the preferred embodiment of the invention illustrated in the figures, the stiffening member 23 is coaxial with the axis of the coiled wire body 14 and surrounds the curve control core wire 17.

A stiffening handle 26 is securely fastened to the proximal end 27 of the stiffening member 23. The stiffening handle 26 serves a similar function as the knob 22 by providing a means for the manipulation of the stiffening member 23 and determines the position of the stiffening member 23 with respect to the cap 12 and with respect to the cylindrical portion 19 of the curve control core wire 17.

It will be understood that the cylindrical portion 19 and the stiffening member 23 have approximately the same outer diameter which is generally the same as the inner diameter of the coiled wire body 14. Also, of course, the core wire 17 has an outer diameter no greater than, and preferably slighter less than the inner diameter of the stiffening member 23.

Suitable manipulation of the components of the multimode guidewire 10 allows selective establishment of a number of regions of flexibility at various locations along the length of the guidewire 10.

In FIG. 1, the curve control core wire 17 is shown placed in close proximity to the cap 12 and the stiffening member 23 is located in near engagement with the curve control core wire 17 in its distal region 18. This configuration results in the guidewire 10 assuming a substantially straight and relatively inflexible mode of use.

In FIG. 2, the stiffening member 23 is shown located in a position establishing a moderately flexible region 28 by proximally moving the stiffening member 23 from the position shown in FIG. 1. As a result, guidewire 10 in FIG. 2 is in a substantially straight moderately flexible mode of use.

In FIG. 3, the curve control core wire 17 is shown retracted to a position in near engagement with the stiffening member 23 to establish a partially curved flexible region 30, adjacent the distal end of guidewire 10. This is accomplished by proximally moving the curve control core wire 17 from the position shown in FIG. 2. This places the guidewire 10 in a mode which can be reasonably characterized as a partially curved relatively inflexible mode of use.

In FIG. 4, the stiffening member 23 is shown proximally withdrawn from near engagement with the cylindrical portion 19 of the curve control core wire 17 to add moderately flexible region 21 to the partially curved flexible region 30. This places the guidewire 10 in a mode which can be characterized as a partially curved moderately flexible mode.

In FIG. 5, the curve control core wire 17 is shown retracted to a position where a rear shoulder 32 of the cylindrical portion 19 engages or is adjacent the distal end coil 25 of the stiffening member 23 so that the distal end flexible region 18 can establish the curved flexible arcuate J-shaped portion 16. This is accomplished by proximally moving both the curve control core wire 17 and the stiffening member 23 from their positions shown in FIG. 3. This places the guidewire 10 in a mode which can be characterized as a curved relatively inflexible mode of use.

In FIG. 6 the guidewire 10 is shown with the moderately flexible region 21 established in the curved guidewire 10 by moving the stiffening member 23 proximally from the position shown in FIG. 5. This places the guidewire 10 in a mode which can be characterized as a curved moderately flexible mode of use.

The ability to select among the several modes of use of the guidewire 10 to establish varying degress of flexibility at varying longitudinal locations naturally lends itself to a method for inserting a catheter using the guidewire 10 into a target cavity through a blood vessel. The method is merely to select one of the modes and distally advance the catheter and the guidewire 10 through the blood vessel so long as the mode of use of the guidewire 10 selected is most appropriate. When another mode of use becomes more appropriate, then the more appropriate mode of use should be selected for advancing the guidewire 10.

For example, where a bend in a blood vessel is encountered while inserting a catheter, the FIG. 3 mode of use or the FIG. 4 mode of use can be utilized to advance the catheter and where a sharper bend is encountered the FIG. 5 or the FIG. 6 mode of use can be utilized to advance the catheter.

It will be apparent from the foregoing description that the multi-mode guidewire 10 of the present invention has a number of advantages, some of which have been described above and others of which are inherent in the invention. Also, it will be apparent that modifications can be made to the multi-mode guidewire 10 of the present invention without departing from the teachings of the invention. Accordingly, the scope of the present invention is only to be limited as necessitated by the accompanying claims.

I claim:

1. A multi-mode guidewire comprising:

elongate flexible means having a lumen generally extending along a longitudinal axis, said flexible means having a proximal end, a distal end and a distal region extending proximally from said distal end, the distal region being predisposed to assume an arcuate shape;

closure means for closing the lumen at the distal end of said flexible means;

elongate rigidifying means disposed within the lumen of said flexible means and slidable therein, said rigidifying means having a proximal end and a distal end and being sufficiently stiff in a distal region of said rigidifying means for reducing the flexibility of said flexible means in the distal region, said rigidifying means having a moderately flexible portion proximately disposed from its distal end just proximal of the distal region of said elongate flexible means;

means fastened to the proximal end of said rigidifying means for controlling the relative position of the distal end of said rigidifying means with respect to said closure means and for altering the rotational position of said rigidifying means;

elongate stiffening means disposed within the lumen of said flexible means and having a proximal end and a distal end, said stiffening means being slidably postionable within the flexible means with respect to the distal end of said rigidifying means, said stiffening means being stiff in its distal region for stiffening the moderately flexible portion of said rigidifying means when said stiffening means is in near engagement with said stiff distal region of said rigidifying means; and means fastened to the proximal end of said stiffening means for controlling the relative position of the distal end of said stiffening means with respect to the distal end of said rigidifying means.

2. A multi-mode guidewire comprising:

an elongate flexible coiled wire body including coils helically wound about a coil axis and defining a longitudinally extending lumen therein, said coiled wire body having a proximal end and a distal end, and being predisposed to assuming an arcuate shape adjacent its distal end;

a cap engaged with the distal end of said coiled wire body;

an elongate curve control core wire disposed within the lumen of said coiled wire body and slidable within the coiled wire body along the coil axis, said curve control core wire having a proximal end and a distal end and being sufficiently stiff in a distal region to overcome the predisposition of the coiled wire body to assume the arcuate shape adjacent the body's distal end, said curve control core wire having a moderately flexible portion just proximal of the stiff distal region of said curve control core wire;

means fastened to the proximal end of said curve control core wire for controlling the relative position of the distal end of said curve contol core wire with respect to said cap;

an elongate stiffening member disposed within the lumen of said coiled wire body and having a proximal end and a distal end, said stiffening member being slidably positionable within the coiled wire body along the coil axis with respect to the distal end of said curve control core wire and being longitudinally stiff at its distal region to stiffen the moderately flexible portion of said curve control core wire when said stiffening member is in near engagement with said distal regon of said curve control core wire; and means fastened to the proximal end of said stiffening member for controlling the relative positon of the distal end of said stiffening member with respect to the distal end of said curve control core wire.

3. The multi-mode guidewire of claim 4 wherein said elongate flexible coiled wire body comprises coiled stainless steel wire coated with a biocompatible plastic.

4. The multi-mode guidewire of claim 1 wherein: said cap has a generally hemispherical portion and a generally cylindrical stem portion and the cylindrical stem portion of said cap is engaged with the distal end of said coiled wire body.

5. The multi-mode guidewire of claim 2 wherein the stiff distal region of said elongate curve control core wire comprises a cylindrical portion which is rounded into a hemispheric shaped end of the same radius as said cylindrical portion at the distal end thereof.

6. The multi-mode guidewire of claim 5 wherein said moderately flexible portion of said core wire comprises a tapered portion having its smallest radius adjacent the cylindrical portion and expanding essentially to a constant radius of said curve control core wire.

7. The multi-mode guidewire of claim 6 wherein said core wire has a diameter less than the diameter of said cylindrical portion and said cylindrical portion has a rear shoulder against which the distal end of said stiffening member can abut.

8. The multi-mode guidewire of claim 2 wherein said elongate curve control core wire is fabricated from stainless steel.

9. The multi-mode guidewire of claim 2 wherein said elongate stiffening member is a helically wound coil wound about said curve control core wire.

10. The multi-mode guidewire of claim 8 wherein said elongate stiffening member is fabricated from stainless steel wire.

11. The multi-mode guidewire of claim 9 wherein said helically wound coil has an inner diameter approximately the same as the outer diameter of said core wire for most of the length of said core wire and an outer diameter approximately the same as the inner diameter of said coiled wire body.

12. The multi-mode guidewire of claim 11 wherein the stiff distal region of said core wire is generally cylindrical and has an outer diameter approximately the same as the inner diameter of the coiled wire body and greater than the outer diameter of the remainder of said core wire and said stiff distal region having a rear shoulder forming a stop for the distal end of said stiffening member.

* * * * *